United States Patent
Brown et al.

(10) Patent No.: US 7,678,548 B2
(45) Date of Patent: Mar. 16, 2010

(54) HIGH THROUGHPUT ASSAY SYSTEMS AND METHODS FOR IDENTIFYING AGENTS THAT ALTER EXPRESSION OF CELLULAR PROTEINS

(75) Inventors: Arthur M. Brown, Brecksville, OH (US); Eckhard Ficker, Cleveland, OH (US); Barbara A. Wible, Cleveland, OH (US)

(73) Assignee: ChanTest, Inc., Cleveland, OH (US)

( * ) Notice: Subject to any disclaimer, the term of this patent is extended or adjusted under 35 U.S.C. 154(b) by 0 days.

(21) Appl. No.: 12/216,579

(22) Filed: Jul. 8, 2008

(65) Prior Publication Data

US 2008/0268472 A1  Oct. 30, 2008

Related U.S. Application Data

(63) Continuation of application No. 10/804,214, filed on Mar. 19, 2004, now abandoned.

(51) Int. Cl.
*G01N 33/53* (2006.01)
(52) U.S. Cl. .............. 435/7.21; 435/7.23; 435/7.24; 435/7.9; 435/366; 435/375; 436/15; 436/55; 436/56; 436/63; 436/64; 436/517; 436/546
(58) Field of Classification Search ............. 435/7.21, 435/7.23, 7.24, 7.9, 29, 2, 366, 375; 436/18, 436/55, 63, 64, 174, 517, 545, 546, 56
See application file for complete search history.

(56) References Cited

U.S. PATENT DOCUMENTS

| | | | |
|---|---|---|---|
| 4,202,896 A | 5/1980 | Gootjes | |
| 4,476,129 A | 10/1984 | Gootjes et al. | |
| 4,874,765 A | 10/1989 | Lapis et al. | |
| 6,187,802 B1 | 2/2001 | Cheetham et al. | |
| 6,303,373 B1 | 10/2001 | Bogan et al. | |
| 6,632,924 B2 | 10/2003 | Bogan et al. | |
| 6,846,643 B2 | 1/2005 | Woska, Jr. et al. | |
| 6,929,923 B2 | 8/2005 | Vallone et al. | |
| 7,211,407 B2 | 5/2007 | Brown et al. | |
| 2002/0068305 A1* | 6/2002 | Woska et al. | 435/7.2 |
| 2002/0150912 A1* | 10/2002 | Owman et al. | 435/6 |
| 2003/0022205 A1* | 1/2003 | Curtis | 435/6 |
| 2004/0018566 A1* | 1/2004 | Vallone et al. | 435/7.21 |

FOREIGN PATENT DOCUMENTS

| | | |
|---|---|---|
| EP | 0 243 903 | 9/2008 |
| WO | 91/01732 | 2/1991 |
| WO | 98/18368 | 5/1998 |

OTHER PUBLICATIONS

Zhang et al., The Extracellular Domain Suppresses Constitutive Activity of the Transmembrane Domain of the Human TSH Receptor: Implications for Hormone-Receptor Interaction and Antagonist Design, Endocrinology 141 (9): 3514-3517 (2000).*
Zhang et al., The Extracellular Domain Suppresses Constitutive Activity of the Transmembrane Domain of the Human TSH Receptor: Implications for Hormone-Receptor Interaction and Antagonist Design, Endocrinology 141 (9): 3514-3517 (2000).
Isacke, Integrin al. The Adhesion Molecule FactsBook, second edition (2000) 149-151.
Maginn et al., "Protective Effects of Vanoxeamine (GBR 12909) Against Ischemia-Induced Hyperactivity and Neurodegeneration in the Gerbil Model of Cerebral Ischemia", Abstract, Pharamacology, Biochemistry and Behavior, 1997, 56(4), pp. 727-735.
Thomas et al., "High-Affinity Blockade of Human Ether-A-Go-Go-Related Gene Human Cardiac Potassium Channels by the Novel Antiarrhythmic Drug BRL-32872", Abstract, Journal of Pharmacology and Experimental Therepeutics, 2001,297(2), pp. 753-761.
Nielsen-Kidsk et al., "Myocardial Accumulation Kinetics and Pharmacodynamics in the Isolated Rabbit Heart of a New Inhibitor of Dopamine Reuptake, GBR 12909," abstract, Pharmacology & Toxicology (Oxford, United Kingdom), 1990, 66(3), pp. 197-202.
W. Tang, et al., "Development and Evaluation of High Throughput Functional Assay Methods for hERG Potassium Channel", Oct. 2001, pp. 325-331, Journal of Biomolecular Screening, vol. 6, No. 5, Bridgewater, NJ.
J. Xu, et al., "Ion-channel Assay Technologies: quo vadis?", Dec. 2001, pp. 1278-1287, Drug Discovery Today, vol. 6, No. 24.
K. Ng et al., "Engineering Protein-Lipid Interactions: Targeting of Histidine-Tagged Proteins to Metal-Chelating Lipid Monolayers", Langmuir, vol. 11, 1995, pp. 4048-4055.
W. Schuhmann et al., "Immobilization of Enzymes on Langmuir-Blodgett Films via a Membrane-Bound Receptor. Possible Applications for Amperometric Biosensors", Advanced Materials, vol. 3, No. 718, 1991, pp. 388-391.

(Continued)

*Primary Examiner*—Gailene R Gabel
(74) *Attorney, Agent, or Firm*—Duane Morris LLP

(57) ABSTRACT

Disclosed are high throughput assay systems and methods for identifying agents that alter the level of expression of proteins in mammalian cells, particularly integral membrane proteins.

15 Claims, No Drawings

OTHER PUBLICATIONS

L. Schmitt et al., "Specific Protein Docking to Chelator Lipid Monolayers Monitored by FT-IR Spectroscopy at the Air-Water Interface", Angewandte Chemie Int. Edition in English, vol. 35, No. 3, 1996, pp. 317-320.

A. Collioud et al., "Oriented and Covalent Immobilization of Target Molecules to Solid Supports, Synthesis and Application of a Light-Activatable and Thiol-Reactive Cross-Linking Reagent", Bioconjugate Chemistry, vol. 4, No. 6, 1993, pp. 528-536.

J. Vandenberg et al., "HERG K+ Channels: friend and foe", Trends Pharmocol. Sciences, vol. 22,2001, pp. 240-246.

M. Roy, Ph.D., et al., "HERG, a Primary Human Ventricular Target of the Nonsedating Antihistamine Terfenadine", Circulation, vol. 94, No. 4, Aug. 1996, pp. 817-823.qa.

K. Finlayson et al., "[3H]Dofetilide Binding to HERG Transfected Membranes: a Potential High Throughput Preclinical screen", Eur. ~ournosf Pharmacology, vol. 430, No. 1, Oct. 2001 ,bp. 147-148.

G. Terstappen, "Functional Analysis of Native and Recombinant Ion Channels Using a High-Capacity Nonradioactive Rubidium Efflux Assay", Analytical Biochemistry, vol. 272, No. 2, Aug. 1999, pp. 149-1 55.

B. Lu et al., "Oriented Immobilization of Fab' Fragments on Silica Surfaces", Analytical Chemistry, II (vol. 67, No. ?, Jan. 1995, pp. 83-87.

A. Iwane et al., "Myosin Subfragment-1 Is Fully Equipped with Factors Essential for Motor Function", Biochemical and Biophysical Research Comm., vol. 230, No. 1, Jan. 1997, pp. 76-80.

W. Frey et al., "Two-Dimensional Protein crystallization via Metal-Ion Coordination by Naturally Occurring Surface Histidines", Proceedings of the Nat'l Academy of Sciences, vol. 93, No. 10, May 1996, pp. 4937-4941.

E. Kubalek et al., "Two Dimensional Crystallization of Histidine-Tagged, HIV-1 Reverse 11 II Transcriptase promoted by a Novel Nickel-Chelating Lipid", Journal of Structural Biology, vol. 113, No. 2. 1994. pp. 117-123.

G. Sigal et al., "A Self-Assembled Monolayer for the Binding and Study of Histidine-Tagged Proteins by Surface Plasmon Resonance", Analytical Chemistry, vol. 68, No. 3, Feb. 1996, pp. 490-497.

Ficker et al, "The Binding Site for Channel Blockers that Rescue Misprocessed Human Long QU Syndrome Type 2 Ether-A-Gogo-Related Gene (HERG) Mutations," abstract, Journal of Biological Chemistry, 2002, 277(7), pp. 4989-4998.

Balser, J. R. et al., "Suppression of time-dependent outward current in Guinea Pia Ventricular Myocytes: Actions of quinidine and amiodarone", Circ. Res. 69:519-529 (1991).

Funck-Bretano, C., "Rate-Dependence of Class III Actions in the Heart", Fundam Clin Pharmacol (1993), 7, 51-59.

Curran, M.E. et al., "A Molecular Basis for Cardiac arrhythmia: HERG Mutations Cause Long QT Syndrome", Cell 80: 795-803 (1 995).

Dutta, A.K. et al., "Positional Importance of the Nitrogen Atom in Novel Piperidine Analogs of GBR 12909: Affinity and Selectivity for the Dopamine Transporter", Medical chemistry Research 3:209-222 (1993).

Hondeghem, L. M., "Development of Class III Antiarrhythmic Agents", J. Cardiovasc. Pharmacol. 20 (SUPPI. 2):S17-S22 (1 992).

Hondeghem, L. M. et al., "Class III Antiarrhythmic Agents Have a Lot of Potential but Long Way to go: reduced effectiveness and dangers of reverse use dependence", Circulation, 81 :686-690 (1990).

Jurkiewicz, N.K. et al., "Rate-Dependent Prolongation of Cardiac Action Potentials by a Methanesulfonanilide Class III Antiarrhythmic Agent: Specific Block of Rapidly Activating Delaved Rectifier K+ Current by Dofetilide", Circ. Res. 72:75-83 (1993).

Lewis, D.B. et al., "Oxygenated Analogues of 1-[2-(Diphenylmethoxy)ethyl]- and 1-[2-[Bis(4- II fluorophenyl)methoxy] ethyl]-4-(3-phenylpropyl)piperazines(~~1~2 935 and GBR i2909) as Potential Extended-Action Cocaine-Abuse Therapeutic Agents", J. Med. Chem. 42:5029-5042 (1999).

Nademanee, K., "The Amiodarone Odyssey", J. Am. Coll. Cardiol. 20:1063-1065 (1992).

Roden, D.M., "Current Status of Class III Antiarrhythmic Drug Therapy", Am. J. Cardiol, 72:44B-49B (1 993).

Sadanaga, T. et al., "Clinical Evaluation of the Use-Dependent QRS Prolongation and the Reverse Use-Dependent QT Prolongation of Class I and Class III Antiarrhythmic Agents and Their Value in Predicting Efficacy", Am. Heart J. 126:114-121 (1993).

Sanguinetti, M.C. et al., "Two Components of Cardiac Delayed Rectifier K+ Current: Differential sensitivity to Block by Class III Antiarrhythmic Agents", J. Gen. Physiol. 96:195-215 (1990).

Singh B.N., et al., "The Effect of Amiodarone, a New Anti-Anginal Drug, on Cardiac Muscle", Br. J. Pharmacol 39:657-667 (1970).

Singh B.N., et al., "A Third Class of Anti-arrhythmic Action. Effects on atrial and ventricular intracellular Potentials, and Other Pharmacological Actions on Cardiac Muscle. of MJ 1999 and At 3474", Br. J. Pharmacol. 39:675-687 (1970).

Williams, E.M., "Classification of Anti-arrhythmic Drugs", Symposium on Cardiac Arrhythmias, (Sandoe E. et al. (Editors))., Chapter 20, pp. 449-472 (1981).

\* cited by examiner

HIGH THROUGHPUT ASSAY SYSTEMS AND METHODS FOR IDENTIFYING AGENTS THAT ALTER EXPRESSION OF CELLULAR PROTEINS

This Application is a Continuation of and claims the benefit of application Ser. No. 10/804,214, filed Mar. 19, 2004, now abandoned the disclosure of which is herein expressly incorporated by reference.

BACKGROUND OF THE INVENTION

1. Field of the Invention

The present invention relates to high throughput assay systems and methods for identifying agents that alter the level of expression of cellular proteins, with special emphasis on integral membrane proteins in mammalian cells.

2. Background of the Related Art

The ability to respond to the surrounding environment and the control of entry and exit of molecules through the cell membrane are fundamentally important functions of any mammalian cell. These functions are due, in significant part, to the various proteins that reside, in whole or in part, within the cell membrane.

The cell membrane of mammalian cells is relatively impermeable to water-soluble substances, such as ions, small inorganic molecules, peptides and proteins. To enter and/or influence a cell, such hydrophilic substances must interact with at least one protein (e.g. a receptor, an ion channel or a transporter) that resides in the cell membrane and is exposed, at least in part, on the cell surface to the extracellular milieu. In contrast, lipophilic substances, such as steroids, can diffuse directly through the cell membrane into the cytoplasm where it can then interact with one or more target proteins.

There are two basic responses from a cell when an external stimulatory molecule (e.g. a peptide or an organic or inorganic molecule) interacts with a cell surface protein: (i) an ionic or molecular (or macromolecular) material is vectorally transmitted from the outside of the cell membrane to the cytoplasm inside the cell by transport through the lipid bilayer and vice versa; and/or (ii) a signal is transmitted to the cytoplasm or a protein therein by virtue of a change in the membrane protein, e.g. a change in the conformation of the membrane protein and/or the state of aggregation of the membrane protein.

The transfer of a signal across the cell (signal transduction) begins with the binding of an extracellular substance (ion, small molecule, protein) to an extracellular domain of a protein resident in the cell membrane. Binding of the substance to an extracellular domain of the transmembrane protein causes the protein to change form an inactive to an active form. This active form then stimulates catalytic activity, or some similar such response, that generates a cytosolic signal (which is sometimes in the form of one or more secondary messenger substances in the cytoplasm).

There are two major types of such signal transduction in mammalian cells: (i) the transmembrane protein may have a protein kinase activity in its cytosolic domain, the activity of which is activated when the extracellular substance binds to the transmembrane protein (the kinase then phosphorylates its own cytoplasmic domain, which enables the transmembrane protein to associate and activate another protein, which in turn acts on other proteins and substances within the cell cytoplasm); and (ii) the transmembrane protein may interact with a G protein that is associated with the membrane, which causes the GDP (guanine diphosphate) bound to the G protein to be replaced by GTP, resulting in dissociation of the G protein into monomer and dimmer fragments, one or both of which, in turn, acts upon a target protein (also often associated with the membrane, requiring it too then to act upon yet another target protein, this one in the cytoplasm).

The physical transfer of material across the cell membrane permits a wide range of substances to get into and/or out of a cell, including ions, small molecules (such as sugars and hormones) and macromolecules (such as proteins and enzymes). Three major routes exist for such material transfer (s): (i) proteins resident in the cell membrane may form channels that permit the passage of ions, such as sodium, potassium and chlorine, from the extracellular milieu through the membrane and into the cytoplasm, or vice versa; (ii) proteins resident in the cell membrane may bind small molecules, such as sugars, on one side of the membrane and then release that same molecule on the opposite side of the membrane, thereby acting as transporters; and (iii) proteins resident in the cell membrane may bind small molecules and so trigger the process of internalization, in which the bound protein:molecule pair is brought into the cell by endocytosis (at some point, the protein:molecule pair becomes separated; the protein may then be returned to the cell surface to interact with another small molecule or it may be degraded).

Common features of all these proteins include their relatively, large size, the multiple hydrophobic regions spanning the cell membrane, and hydrophilic extracellular and/or intracellular domains.

With respect to the passage or trafficking of macromolecular substances, proteins begin the pathway that leads to secretion by co-translational transfer directly from ribosomes to the membranes of the endoplasmic reticulum. These proteins are then transferred to the Golgi apparatus, where they are sorted according to their final intended destination and move towards the cell membrane.

More specifically, proteins enter the ER during synthesis and are folded and glycosylated, at least partially. The proteins are then transferred to the cis face of the Golgi apparatus (proteins that are to be resident in the endoplasmic reticuluim are returned to the ER at this time). Further glycosylation occurs as the proteins move through the Golgi stacks from cis to trans. Specific signals cause some proteins to be returned to the ER, some proteins to be retained in the Golgi, some proteins to be transported to endosomes and lysosomes, and some proteins (cell surface proteins) to be transported to and retained in the cell membrane.

Those proteins that are transported to and retained in the cell membrane follow the longest and most extensive trafficking pathway, entering the membranes of the endoplasmic reticulum and subsequently traveling through the membranes of transition vesicles, the Golgi complex and secretory vesicles before reaching their final destination. Among these proteins are active and passive transport proteins and cell surface receptors.

To illustrate the complexity of the trafficking pathway, in epithelial cells lining body cavities, the sorting and distribution mechanism of the ER places different proteins in distinct subparts of the cell membrane. For example, proteins transporting sugars and amino acids in intestinal epithelial cells are distributed to that region of the cell membrane facing the intestinal cavity. MHC molecules and the poly-Ig receptors binding antibodies wind up in segments of the cell membrane of epithelial cells on the side opposite the side facing the body interior.

The following is a table of some known cell surface molecules, receptors and membrane-associated proteins.

| | |
|---|---|
| EGFR | epidermal growth factor receptor |
| β-adrenoreceptor | GPCR |
| GABAaR | GABAa-gated ion channel |
| nAChR | ACh-gated ion channel |
| P-glycoprotein | membrane channel |
| Kir2.2 | ion channel |
| MCR | melanocortin receptor |
| hERG | ion channel |
| A4 | TM4 family |
| Abc2 | ABC transporter; multi-tm; mdr subfamily |
| AcPL | required for IL-18 receptor signaling. Contains two Ig domains |
| AF1q | fused to MLL in some leukemias |
| Alpha-6 integrin | complex with NAG-2 |
| Alpha-9 integrin | Mediates cell-cell and cell-extracellular matrix interactions |
| ART-4 | Adenocarcinoma antigen recognized by T-lymphocytes |
| B29 | Ig superfamily |
| BAP31 | potential membrane protein |
| Beta ig-h3 | TGF-beta induced; may be associated with microfibrils and the cell surface |
| Bgpd | May play role in self-renewal/diff. of epithelia |
| Catechol-O-methyltransferase | membrane-bound form; inactivates catecholamine neurotransmitters |
| CD9 | TM4; with CD19 in multimolecular B1-integrin complex, also NAG-2 |
| CD19 | Ig domains; B-cell growth regulation |
| CD27 | receptor for CD70; TNFR-family; apoptosis |
| CD31/PECAM-1 | adhesion molecule |
| CD34 | "Stem cell antigen" |
| CD37 | TM4 on B-cells |
| CD48 | ligand for CD2 |
| CD53 | TM4 superfamily; high in Burkitt lymphoma cell lines |
| CD54/ICAM-1 | adhesion molecule |
| CD59 | complement inhibitory protein |
| CD69 | Involved in lymphocyte proliferation |
| CD87/PAR2 | Urokinase plasminogen activator receptor |
| CG1 | Possible TM4 cell surface protein |
| Coronin-2 | WD40 domain |
| DPH2L | single tm; ovarian ca. suppressor |
| DR5 | Death receptor for TRAIL; apoptosis-inducing |
| EBI1 | 7-tm receptor |
| EBI3 | contains FnIII domain |
| EP2 or -4 | prostanoid receptor |
| Evi2B | Implicated in leukemogenesis |
| FC gamma R I | Antibody Fc receptor |
| FZD4 | Frizzled 4; receptor for Wnt family ligands |
| Flk-2 | receptor tyrosine kinase; differentially expressed |
| Flotillin | BAND7 family |
| GITR | glucocorticoid-induced; TNFR family; apoptosis assoc |
| GluR3 | Glutamate Receptor |
| Glypican | Major heparan sulfate proteoglycan |
| GPCR | Orphan G-protein coupled receptor |
| GPR-9-6/CCR9 | orphan 7-tm hormone receptor |
| HEM-1 | TM4 family |
| Hepatocyte GF activator inhibitor | membrane-bound form |
| IB3089A | Putative transmembrane protein |
| ICAM-2 | Intercellular adhesion molecule |
| IL-2-gamma | common chain for IL2 and 4 and 7 and 13 |
| IL-3-beta | common to IL3 and 5 R |
| IL-3R | Hematopoietic growth factor receptor associated with survival and differentiation |
| IL-4-alpha | mature form includes IL2 gamma chain |
| IL-6R | Hematopoietic growth factor receptor |
| IL-7R | B-cell growth factor |
| JTB | Cell surface protein; rearranged in a jumping translocation |
| L-selectin | lymphocyte homing molecule |
| LAPTm5 | may have functional role in embryogenesis |
| Ligatin | trafficking receptor for phosphoglycoproteins |
| LOX-1 | Lectin-like oxidized low-density lipoprotein receptor |
| LSM-1 | interacts with CD45 on lymphocytes |
| Lymphotoxin-b R | poss. function in immune development |
| Mac-2 | |
| Mama | Scavenger-like Cys-rich domain |
| Mb-1 | supposedly B-cell restricted; CD3-like |
| Mcp-1 | chemokine R |
| MDC15 | metalloprotease-disintegrin; tm glycoprotein |
| MEGF9 | EGF repeats |
| MIP-1aR | chemokine R |
| Mitsugumin 23 | TM4 protein on ER and nuclear membranes |
| MP70 | 9 tm |
| NAG-2 | Surface TM4 protein similar to CD53; forms complexes w/integrins |
| NET-4 | TM4 protein |
| NET-6 | TM4 protein |
| Neuropilin | Semaphorin III receptor; also binds VEGF |
| NHE-1 | sodium/hydrogen antiporter |
| Notch-1 | Required for the correct differentiation of many tissues |
| PAR-1 or -2 | Plasminogen activator receptor |
| perlecan | basement membrane heparan sulfate proteoglycan |
| Pft27 | Putative 7-tm receptor |
| PIRA-1 | Ig-like; suggested immune regulatory role |
| Prostaglandin E R | 7-tm receptor |
| Protocadherin-2C | Expressed in developing brain |
| RPTP-sigma | receptor tyrosine phosphatase; contains Fn III domains |
| Selenoprotein R | Putative; contains domain of unknown function |
| Semaphorin B | Growth cone guidance protein |
| SIM | stromal cell protein; TM4 surface R |
| Smoothened | Recptor for Sonic Hedgehog; 7-tm |
| Sortilin | neurotensin R (NT converting enzyme is in stroma) |
| Stromal Cell Protein | Potential TM4 cell surface protein |
| SYBL1 | synaptobrevin-like |
| TLR2 | Toll-like receptor 2 |
| TLR4 | Toll-like receptor 4 |
| TSA-1 (Sca-2) | Thymic shared antigen; also called Ly-6E |
| Tspan6 | TM4 superfamily; unknown function |

The identification of compounds that alter the level of expression of one or more of these proteins is therefore quite important from a number of different perspectives and with a number of goals in mind. For example, identifying a compound that alters the level of expression of a particular protein may lead to the discovery of new therapeutic agents. Alternatively, such an identification may lead to the discovery of the cause or pathway of a defect or disorder. In that way, entirely new areas of research are opened up, as well as a wealth of previously-unknown targets for potential therapeutic intervention.

Moreover, the identification of compounds that alter the level of expression of one or more of these proteins should include compounds that directly or indirectly affect the level of protein expression. A compound that alters the level of expression of an integral membrane protein may do so directly, for example, by binding directly to the protein and inhibiting trafficking. Alternatively, a compound may alter the level indirectly, for example by acting on one or the chaperones that facilitate transport and integration of membrane proteins in the cell membrane or by acting on a protein that degrades the target membrane protein.

There therefore exists a need in the art for assays that can identify compounds that alter the level of expression of proteins, particularly integral membrane proteins, as well as the mechanism by which that level is altered.

SUMMARY OF THE INVENTION

It is therefore an object of the present invention to provide assays and methods for identifying agents that alter the level of expression of proteins, particularly integral membrane proteins such as cardiac ion channels. Such agents may be compounds from chemical libraries or peptides from DNA libraries.

In accordance with these and other objects, a first embodiment of the present invention is directed to a method for identifying an agent that alters the level of expression of a protein on the surface of a mammalian cell, comprising: a) preparing a medium containing mammalian cells that express a protein of interest; b) adding an effective amount of a candidate agent; c) incubating the cells in the presence of the candidate agent for a sufficient period of time; d) treating the cells with a fixtive; e) adding an effective amount of at least one antibody which binds to the protein; and f) determining the level of binding, wherein a change in the level of binding indicates that the candidate agent alters the level of expression of the protein.

A second embodiment of the present invention is directed to a method for identifying an agent that alters the level of total expression of a protein in a mammalian cell, comprising: a) preparing a medium containing mammalian cells that express a protein of interest; b) adding an effective amount of a candidate agent; c) incubating the cells in the presence of the candidate agent for a sufficient period of time; d) treating the cells with a fixative followed by a permeabilizing agent; e) adding an effective amount of at least one antibody which binds to the protein; and f) determining the level of binding, wherein a change in the level of binding indicates that the candidate agent alters the level of expression of the protein.

A third embodiment of the present invention is directed to a method for identifying an agent that blocks an ion channel in a mammalian cell, comprising: (i) performing the method of the first embodiment of the present invention described above to determine if the agent alters the level of expression of the ion channel; (ii) performing a Western blot assay to determine if the agent alters maturation of the ion channel; and (iii) performing a tail current assay to determine if the agent alters the functional effect of the ion channel.

Additional advantages, objects and feature of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

DETAILED DESCRIPTION OF PREFERRED EMBODIMENTS

Preferred embodiments of the present invention include an assay system and method for identifying an agent that binds to a protein, such as a membrane ion channel, and thereby increases or decreases its expression in mammalian cells. In certain particularly preferred embodiments, the assay and system determine the ability of an agent to bind to a protein and thereby alter the surface expression thereof. Such an alteration in surface expression may result from the agent binding to a particular site on the protein and/or from the agent reducing or improving intracellular trafficking and/or processing of the protein. Moreover, such an alteration may also result from the agent binding to a protein other than the protein of interest and thereby indirectly altering the level of expression of the protein.

There are a wide variety of formats known and available to those skilled in the art for appropriate binding assays. According to certain embodiments of the present invention, one or more cells expressing a protein of interest may be provided in a suitable liquid medium and exposed to one or more candidate compounds, while in other embodiments the cells may be immobilized on a surface. Similarly, according to still other embodiments of the invention, one or more candidate compounds may be immobilized on a surface and exposed to a liquid medium containing one or more cells that express a protein of interest or the candidate compound(s) may be included in a suitable liquid medium to which one or more cells expressing a protein of interest is added.

Binding is often easier to detect in systems in which at least one of the candidate compound and the protein of interest is labeled (e.g., with fluorescence, radioactivity, an enzyme, an antibody, etc., including combinations thereof, as known to those skilled in the art). After exposing the candidate compound to the cell expressing a protein and washing off or otherwise removing unbound reagents, the presence of the labeled moiety (i.e., bound to the unlabelled component of the test system) is measured.

Methods for performing various binding assays are known in the art, including but not limited to the assay systems such as those described in PCT Application U.S. 98/18368. Various references provide general descriptions of various formats for protein binding assays, including competitive binding assays and direct binding assays, (see e.g., Stites and Terr, *Basic and Clinical Immunology, 7th ed*. (1991); Maggio, *Enzyme Immunoassay*, CRC Press, Boca Raton, Fla. (1980); and Tijssen, *Practice and TheoLy of Enzyme Immunoassqys*, in *Laboratory Teelmiques in Biochemistry and Molecular Biology*, Elsevier Science Publishers, B. V. Amsterdam, (1985)).

Particularly preferred embodiments of the present invention involve assay systems and methods to identify compounds that increase or decrease the expression of a protein of interest by altering the activity of the protein and/or by altering (blocking or improving) intracellular trafficking and/or processing thereof.

Thus, according to certain particularly preferred embodiments, immunoassays are provided in which one or more cells expressing a protein of interest are generally bound to a suitable solid support (e.g. the well of a microtiter plate, a microcard, or any other similar format known to those skilled in the art) and combined with a candidate agent, and observing changes in the level of expression of the protein of interest. Thus, in these preferred embodiments, one or more of the assay components are attached to a solid surface.

According to certain embodiments, for example when the protein of interest is not expressed on the surface of the cells, a permeabilizing agent may be used. Such a permeabilizing agent may facilitate penetration of an antibody, particularly a labeled antibody, into the cell.

The permeabilizing agent preferably contains a detergent, more preferably an anionic detergent. Suitable detergents are known and available to those skilled in the art. Illustrative examples of suitable anionic detergents include, for example, sodium dioxycholate, N-lauryl sarcoside and sodium dodecyl sulphate.

The concentration of detergent will vary depending upon, for example, the particular detergent employed and may be determined empirically by one skilled in the art. Suitable concentrations can be between 0.001% and 10%, for example between 0.01 and 5%.

The permeabilizing agent also preferably contains an oligosaccharide, such as trehalose. The concentration of oligosaccharide in the permeabilizing agent will vary depending upon, for example, the particular detergent and oligosaccharide employed and may be determined empirically by one skilled in the art. Illustrative examples of suitable concentrations are in the range from 0.001 M and 1.0 M, preferably in the range between 0.01 M and 0.1 M.

The pH of the permeabilizing agent may be any level appropriate for the particular protein being studied and cell line employed, and is preferably generally between 3 and 8. A suitable pH (or pH range) may be achieved by the addition of one or suitable buffers known and available to those skilled in the art.

The permeabilizing buffer is preferably approximately isotonic and may contain one or more suitable agents for adjusting the isotonicity thereof, such as sodium chloride.

In some embodiments, an assay system may be used (as known in the art) to detect the change in the surface expression of the protein of interest due to the binding of the candidate agent. For example, if the protein of interest is a membrane ion channel, a patch clamp assay may be employed to detect a change in the flux of ions across the membrane, which may indicate an increase in the level of surface expression of the ion channel.

In alternative embodiments, an indirect immunoassay system is used in which the protein is detected by the addition of one or more antibodies directed against an epitope of the protein, as known in the art. If the protein is not expressed on the surface of the cell, it may be desirable to add a permeabilizing agent to facilitate penetration of the antibody into the cell.

When using a solid support in the methods of the present invention, virtually any solid surface is suitable, as long as the surface material is compatible with the assay reagents and it is possible to attach the component to the surface without unduly altering the reactivity of the assay components. Those of skill in the art recognize that some components exhibit reduced activity in solid phase assays, but this is generally acceptable, as long as the activity is sufficient to be detected and/or quantified.

Suitable solid supports include, but are not limited to, any solid surface such as glass beads, planar glasses, controlled pore glasses, plastic porous plastic metals, or resins to which a material or cell may be adhered, etc.). Those of skill in the art recognize that in some embodiments, the solid supports used in the methods of the present invention may be derivatized with functional groups (eg, hydroxyls, amines, carboxyls, esters, and sulfhydryls) to provide reactive sites for the attachment of linkers or the direct attachment of the candidate agent or other assay component.

Adhesion of an assay component to a solid support can be direct (i.e. the component directly contacts the solid surface) or indirect (i.e. an agent and/or component (e.g. an antibody) is/are bound to a support, and the other assay component(s) binds to this agent or component rather than to the solid support). In some embodiments, the agent or component is covalently immobilized (e.g., utilizing single reactive thiol groups of cysteine for anchoring proteinaceous components (see e.g., *Bioconjug. Chem.*, 4:528-536 (1993)), or non-covalently, but specifically.(e.g., via immobilized antibodies or other specific binding proteins (see e.g., *Adv. Mater.*, 3:388-391 (1991); *Anal. Chem.*, 67:83-87 (1995))), the biotin/streptavidin system (see e.g., *Biophys. Biochem. Res. Commun.*, 230:76-80 (1997)), or metal-chelating Langmuir-Blodgett films (see e.g., *Langmuir* 11:4048-4055 (1995); *Angew. Chem. Int. Ed. Engl.*, 35:317-320 (1996); *Proc. Natl. Acad. Sci.* USA 93:4937-4941 (1996); and *J. Struct. Biol.*, 113:117-123 (1994)), and metal-chelating self-assembled monolayers (see e.g., *Anal Chem.*, 68:490-497 (1996)), for binding of polyhistidine fusion proteins.

In some particularly preferred embodiments, standard direct or indirect ELISA, IFA, or RIA methods as generally known in the art are used to detect the binding of a candidate agent to a protein of interest. In some embodiments, an increase in the level of surface expression of the protein is detected in a sample, while in other embodiments, a decrease in the level of surface expression is detected. Thus, it is clear that the methods of the present invention are adaptable to the detection, identification, and characterization of multiple elements.

Accordingly, in some particularly preferred embodiments of the methods of the present invention, a sandwich ELISA (enzyme-linked immunosorbent assay) with a monoclonal or polyclonal antibody for capture (Aa capture antibody) and a secondary antibody (Aa reporter antibody) for detection of bound antibody-antigen complex may be used.

In some preferred ELISA embodiments, alkaline phosphatase conjugates are used, while in still other preferred embodiments, horseradish peroxidase conjugates are used. In addition, avidin/biotin systems may also be used, particularly for assay systems in which increased signal is desired. Suitable enzymes for use in preferred embodiments include, but are not limited to, peroxidases, luciferases, alkaline phosphatases, glucose oxidases, beta-galactosidases and mixtures of two or more thereof.

According to certain embodiments of the present invention, the cells may be treated with a fixative before addition of antibody or antibodies. Suitable such fixatives are known and available to those skilled in the art, and include, but are not limited to, paraformaldehyde, formalin, gluteraldehyde, acetone, ethanol and acrolein. See, e.g. U.S. Pat. Nos. 4,857,300; 5,104,640; 5,422,277; 5,597,688; 5,824,495; and 6,194,165.

The concentration of fixative will vary depending upon, for example, the particular agent employed and may be determined empirically by one skilled in the art. An illustrative example of a suitable concentration of paraformaldehyde would be 4% in a suitable buffer such as phosphate buffered saline (PBS).

The pH of the fixative may be any level appropriate for the particular protein being studied and cell line employed, and is may generally be between 6 and 8, for example around 7, such as about 7.2. A suitable pH (or pH range) may be achieved by the addition of one or suitable buffers known and available to those skilled in the art.

Thus, in one illustrative method of the present invention, a cell line overexpressing the potassium channel HERG with an HA tag in an extracellular epitope is plated in a 96-well microplate (~40,000 cells/well). The 96-well plate (black plate with clear bottom) is precoated with poly-D-lysine to facilitate attachment of the cells to the bottom of the wells. The cells are plated in complete medium consisting of DMEM/F12 with 10% fetal bovine serum (FBS) plus antibiotics. Approximately 6 hours after plating, the media is removed, the wells rinsed with DMEM/F12 without serum or antibiotics, and test articles (diluted in serum- and antibiotic-free DMEM/F12) applied. Test articles are most often dissolved in DMSO, and the final concentration of DMSO in the assay is 0.1%. Vehicle controls also contain 0.1% DMSO. The plates are incubated overnight (approximately 16 hours) at 37° C./5% $CO_2$ prior to the start of the surface expression assay.

Surface expression assays are preferably performed on the bench top at room temperature. The cells are rinsed three times with PBS (phosphate buffered saline), followed by fixation with freshly prepared ice-cold 4% paraformaldehyde in PBS (pH 7.2, 20 minutes). For determination of hERG surface expression, the cells are not permeabilized. Following removal of the fixative, the cells are washed with PBS. Non-specific binding sites on the cells are blocked by incubation with 1% goat serum in PBS (blocking buffer) for 30 minutes. The blocking buffer is removed, and the cells incubated for two hours with rat anti-HA antibody (primary antibody) diluted in blocking buffer. After removing the primary antibody, the cells are washed three times with 1% goat serum in PBS (10 min/wash). HRP-conjugated goat anti-rat antibody (secondary antibody) is diluted in blocking buffer and incubated with the cells for one hour. The secondary antibody cocktail also contains a fluorescent DNA binding dye (SYBR Green) to determine cell number at the end of the protocol. Following incubation, cells are washed three times with PBS (10 min/wash). Fluorescence is measured in a microplate fluorescence reader, and signals compared to a standard curve of fluorescence versus cell number to determine whether test articles are toxic and to correct for loss of cells during the protocol. Chemiluminescent signals are developed with the SuperSignal ELISA Femto Maximum Sensitivity Substrate (Pierce Chemical Co). PBS is removed from the wells, and the detection reagent added. Signals are captured immediately with a GloRunner luminometer.

An additional step may be added to examine total cellular expression of an integral membrane protein or any intracellular protein. Following fixation, a permeabilizing agent (e.g., a detergent) may be used to facilitate access of the antibody to the intracellular protein.

According to a first particularly preferred embodiment of the present invention, a method is provided for identifying an agent, such as a peptide, protein, antibody or chemical agent, that alters the level of surface expression of a protein, preferably an integral membrane protein, such as hERG, in a mammalian cell. This method comprises: a) preparing a first medium containing mammalian cells that express the protein of interest; b) adding an effective amount of a candidate agent; c) incubating the cells in the presence of the candidate agent for a sufficient period of time; d) adding an effective amount of at least one antibody which binds to at least one extracellular epitope of the protein; and e) determining the level of binding of the antibody to the extracellular epitope of the protein following incubation of the cells with the candidate agent.

Any change, such as an increase or decrease, in the level of binding in the presence of the candidate agent relative to control indicates that the candidate agent alters the level of surface expression of the protein.

According to preferred embodiments of the present invention, step (d) above comprises adding an effective amount of at least one primary antibody and an effective amount of at least one secondary antibody. According to such embodiments, the primary antibody preferably binds to at least one extracellular epitope of the protein of interest. Even more preferably, according to such embodiments, the secondary antibody binds to the first antibody.

Preferably, the primary antibody and/or the secondary antibody is coupled to an enzyme to facilitate detection and determination of the level of binding. Suitable enzymes for use in the methods of the present invention are known and available to those skilled in the art. Illustrative examples of suitable enzymes include, but are not limited to, peroxidases, luciferases, alkaline phosphatases; glucose oxidases, beta-galactosidases and mixtures of two or more thereof.

The determination of the level of surface expression of the protein of interest may be performed using any of the methods and techniques known and available to those skilled in the art. Preferably, the level of binding is determined by fluorescence, luminescence, radioactivity, absorbance or a combination of two or more of these.

According to preferred embodiments of the present invention, the extracellular epitope to which the antibody binds on the membrane protein is preferably a wild-type epitope, i.e. an extracellular epitope normally found on the naturally-occurring form(s) of the protein of interest.

According to particularly preferred embodiments of the present invention, the extracellular epitope on the membrane protein contains a tag. Suitable tags are known and available to those skilled in the art. A particularly preferred tag for use in the methods of the present invention is a hemagglutinin (HA) tag. The tag may be inserted in an extracellular domain of the protein or may replace a portion of an extracellular domain thereof.

For purposes of illustration and not limitation, in a preferred embodiment of the present invention, an ion channel, such as HERG, is engineered to express an extracellular tag, such as an HA tag, in the linker between transmembrane domains S1 and S2 (such a tag preferably should not alter the functional properties of the channel). Cells, such as HEK 293 cells, stably expressing this tagged protein are plated in a suitable container, such as a 96-well microtiter plate, and incubated with one or more candidate agents for a sufficient time, such as overnight. The cells are then preferably fixed, such as with formaldehyde, but preferably not permeabilized, and antibodies recognizing the HA tag are added. A secondary antibody, preferably conjugated to an enzyme, such as horseradish peroxidase, is used to bind the anti-HA antibody (ies) bound to the surfaces of the fixed cells. Cell surface signals may then be developed by any suitable method, such as a chemiluminescent reaction mix, and the level measured, for example, in a microtiter plate luminometer. Control cells are usually incubated with water and/or any liquid vehicle used in conjunction with the candidate agent, such as DMSO.

According to more particularly preferred embodiments of the above methods, protein surface expression is assayed by removing the microtiter plate(s) from the incubator(s) and removing the media bathing the cells. The wells are rinsed three times with PBS (100 µl) and then the cell fixed with paraformaldehyde (e.g. 4% in PBS, pH 7.2, 100 µl), and then rinsed with PBS. Non-specific binding sites on the cell surface are preferably blocked, for example by incubating the cells with 1% goat serum in PBS ("blocking buffer"). After removing the blocking buffer, the cells are incubated with the primary antibody, such as rat anti-HA in blocking buffer. The primary antibody is then removed, the cells washed (e.g. 3 times with blocking buffer). Secondary antibody, such as horseradish peroxidase-conjugated anti-rat goat antibody in blocking buffer, is added. The secondary antibody is then removed and the cells preferably washed.

According to such embodiments, chemiluminescent signals may be developed using any suitable technique, such as SuperSignal ELISA Femto Maximum Sensitivity Substrate (Pierce Chemical Co.). A suitable amount of reagent, e.g. 50 µl for each well of a microtiter plate, is added and a GloRunner luminometer (Turner Designs) used to obtain the data.

A fluorescent reaction may optionally be added to monitor the number of cells per well.

By employing certain embodiments of the present invention, peptides may be identified that affect expression of integral membrane proteins. For example, a retroviral expression library generated from human heart may be used to deliver genes stably into mutant hERG parent cell lines at an MOI (multiplicity of infection) of approximately one. Two days after infection, live cells will be labeled with HA-specific primary antibody followed by FITC-conjugated secondary antibody. Fluorescent cells will be sorted with a fluorescence-activated cell sorter (FACS) for an increase in cell surface expression of hERG protein when compared to parent cell lines. The sorted cell population will be expanded for several days and then re-sorted for a second time applying the above described selection criteria. Cell clones with permanently altered surface staining will be used to capture the transforming gene. PCR reactions will be performed on genomic DNA using vector specific primers flanking the cloning site.

To look for differences, genomic DNA will be isolated from FACS-sorted cells with increased surface expression and from parent clones, which will be used as control templates in PCR reactions. PCR products will be subcloned into the pCR-II-TOPO vector and sequenced. Clones isolated in this screen will be tested for their ability to modulate cell surface expression of hERG protein in electrophysiological and Western blot experiments using mammalian expression vectors in transient transfections. Thus, genes crucial for biogenesis and post-translational processing of trafficking competent hERG proteins may be identified.

The basic procedures of immunostaining live cells for FACS are described in Ficker et. al., *Am J. Physiol.* 2000; 279:H1748-H1756 and Ficker et. al., *J Mol Cell Cardial.* 2000; 32:2327-2337. For virus production, AmphoPack-293 cells (Clontech) are plated at a density of $5 \times 10^6$ cells on 100 mm dishes. After 48 h 10 µg of plasmid library DNA (Viraport Human Heart Retroviral Expression Library, Stratagene) is mixed with Fugene as recommended by the manufacturer (Roche Biochemicals) and added to the culture dish in the presence of serum. Since there is no selection marker in the retroviral vector DNA, transduction efficiency and viral titer are determined by monitoring fluorescent cells on control plates transduced with a virus expressing enhanced green fluorescent protein EGFP (Clontech). COS-7 cells ($10^6$) expressing HA-tagged hERG WT S1HAS2 channel protein at moderate levels are suspended in 5-10 ml DMEM, infected with viral supernatant at an MOI (multiplicity of infection) of approximately 1 and plated in 100 mm cultures dishes. After several hours, the medium is replaced with complete DMEM. After two days, cells are labeled with anti HA antibody, followed by a FITC conjugated secondary antibody (see above) and sorted with a fluorescent activated cell sorter. Cells showing significant changes in surface fluorescence when compared to parent cell line are first expanded for ten days and then sorted for a second time. Genomic DNA is isolated from the twice-sorted cell population and PCR reactions are performed using vector-specific primers to capture library inserts.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of identifying an agent that alters the level of surface expression of a membrane ion channel in a mammalian cell, said method comprising:
    a) preparing a medium containing mammalian cells that express said membrane ion channel;
    b) adding to said medium containing mammalian cells a test amount of a candidate agent;
    c) incubating said cells in the presence of said candidate agent for at least 16 hours;
    d) treating said cells with an amount of a fixative effective to stabilize said cells for subsequent processing and examination;
    e) adding to said medium containing mammalian cells, candidate agent and fixative of step (d) at least one antibody which binds to at least one extracellular epitope of said membrane ion channel in an amount effective to measurably bind to said membrane ion channel wherein said extracellular epitope contains a tag; and
    f) detecting the level of binding of said antibody to said at least one extracellular epitope of said membrane ion channel with said candidate agent, wherein a change in said level of binding relative to control indicates that said candidate agent alters the level of surface expression of said membrane ion channel, wherein said control comprises said medium containing mammalian cells that express said membrane ion channel in an amount equal to that in step (a) and said at least one antibody in an amount equal to that added in step (e).

2. The method according to claim 1, wherein step (e) comprises adding at least one primary antibody followed by an approximately equal amount of at least one secondary antibody, wherein said primary antibody binds to at least one extracellular epitope of said membrane ion channel and said secondary antibody binds to said first antibody.

3. The method according to claim 2, wherein said at least one extracellular epitope comprises a wild-type epitope.

4. The method according to claim 1, wherein said level of binding is measured by fluorescence, luminescence, radioactivity, absorbance or a combination of two or more thereof.

5. The method according to claim 1, wherein said extracellular tag replaces at least a portion of an extracellular domain of said membrane ion channel.

6. The method according to claim 5, wherein said extracellular tag is inserted in an extracellular domain of said membrane ion channel.

7. The method according to claim 1, wherein said extracellular tag comprises a hemagglutinin (HA) tag.

8. The method according to claim 1, wherein said antibody is coupled to an enzyme.

9. The method according to claim 8 wherein said enzyme is selected from the group consisting of peroxidases, luciferases, alkaline phosphatases, glucose oxidases, beta-galactosidases and mixtures of two or more thereof.

10. The method according to claim 1, wherein said tag in said extracellular epitope is the only tag present on said membrane ion channel.

11. The method according to claim 1, wherein said membrane ion channel contains a fluorescent tag.

12. The method according to claim 11, wherein said tag is selected from the group consisting of Green Fluorescent Protein, Red Fluorescent Protein, and Blue Fluorescent Protein.

13. The method according to claim 12, wherein said tag replaces at least a portion of an intracellular domain of said membrane ion channel.

14. The method according to claim 12, wherein said tag is inserted in an intracellular domain of said membrane ion channel.

15. The method according to claim 13 or 14, wherein said tag in said intracellular domain is the only tag present on said membrane ion channel.

* * * * *